(12) United States Patent
Ma et al.

(10) Patent No.: US 11,707,603 B2
(45) Date of Patent: Jul. 25, 2023

(54) INTRAVENOUS THERAPY SYSTEM FOR BLOOD VESSEL DETECTION

(71) Applicant: Becton, Dickinson and Company, Franklin Lakes, NJ (US)

(72) Inventors: Yiping Ma, Layton, UT (US); Kathryn Willybiro, Park City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 796 days.

(21) Appl. No.: 16/742,035

(22) Filed: Jan. 14, 2020

(65) Prior Publication Data
US 2020/0230365 A1 Jul. 23, 2020

Related U.S. Application Data

(60) Provisional application No. 62/794,442, filed on Jan. 18, 2019.

(51) Int. Cl.
*A61M 25/06* (2006.01)
*A61B 5/15* (2006.01)
(Continued)

(52) U.S. Cl.
CPC ....... *A61M 25/0606* (2013.01); *A61B 5/0086* (2013.01); *A61B 5/15003* (2013.01);
(Continued)

(58) Field of Classification Search
CPC .......... A61M 25/0606; A61M 2205/13; A61M 2205/3313; A61M 2205/581; A61M 2205/583; A61M 2205/587; A61M 2205/50; A61M 2205/502; A61M 2207/00; A61M 5/427; A61B 5/0086; A61B 5/15003; A61B 5/150389;
(Continued)

(56) References Cited

U.S. PATENT DOCUMENTS 5,036,853 A * 8/1991 Jeffcoat ............... A61B 5/0084
600/478
5,769,791 A * 6/1998 Benaron ............ A61B 17/3417
600/476
(Continued)

FOREIGN PATENT DOCUMENTS

| EP | 2710974 | 3/2014 | |
|---|---|---|---|
| RU | 159678 | 2/2016 | |
| WO | WO-2007032992 A1 * | 3/2007 | ......... A61B 5/15003 |
| WO | WO-2009037432 A1 * | 3/2009 | ........... A61B 5/0059 |
| WO | WO-2013163443 A2 * | 10/2013 | ........... A61B 5/0013 |

*Primary Examiner* — Matthew Kremer
*Assistant Examiner* — Om Patel
(74) *Attorney, Agent, or Firm* — Kirton McConkie; Whitney Blair; Kevin Stinger

(57) ABSTRACT

An intravenous therapy system may include a hollow needle comprising a distal end and a proximal end, the distal end comprising a sharp tip for insertion into a vein; an infrared (IR) camera placed within a hollow portion of the hollow needle, including: an IR detector; a first light source to emit a first wavelength of IR light; and a second light source to emit a second wavelength of IR light; a comparator to, upon execution of a processor communicatively coupled to the comparator, compare an amount of reflected light received at the IR detector during activation of the first light and second light and provide an indication of light absorption within a vein.

16 Claims, 7 Drawing Sheets

(51) Int. Cl.
*A61B 5/153* (2006.01)
*A61B 5/00* (2006.01)

(52) U.S. Cl.
CPC ...... *A61B 5/1535* (2013.01); *A61B 5/150389* (2013.01); *A61B 5/150824* (2013.01); *A61B 5/6848* (2013.01); *A61M 2205/13* (2013.01); *A61M 2205/3313* (2013.01); *A61M 2205/581* (2013.01); *A61M 2205/583* (2013.01); *A61M 2205/587* (2013.01)

(58) Field of Classification Search
CPC ............ A61B 5/150824; A61B 5/1535; A61B 5/6848; A61B 34/20; A61B 5/150503; A61B 5/150748; A61B 5/065; A61B 5/489
See application file for complete search history.

(56) References Cited

U.S. PATENT DOCUMENTS

| | | | |
|---|---|---|---|
| 7,729,735 B1 | 6/2010 | Burchman | |
| 2004/0019280 A1* | 1/2004 | Waner | A61M 25/0017 600/466 |
| 2014/0100524 A1 | 4/2014 | Zarei et al. | |
| 2014/0100550 A1* | 4/2014 | Zarei Mahmoodabadi | A61B 17/3403 604/528 |
| 2015/0065916 A1 | 3/2015 | Maguire et al. | |
| 2016/0256101 A1* | 9/2016 | Aharoni | A61B 5/0086 |
| 2017/0319825 A1 | 11/2017 | Gasparyan et al. | |
| 2018/0133411 A1 | 5/2018 | Yu | |

* cited by examiner

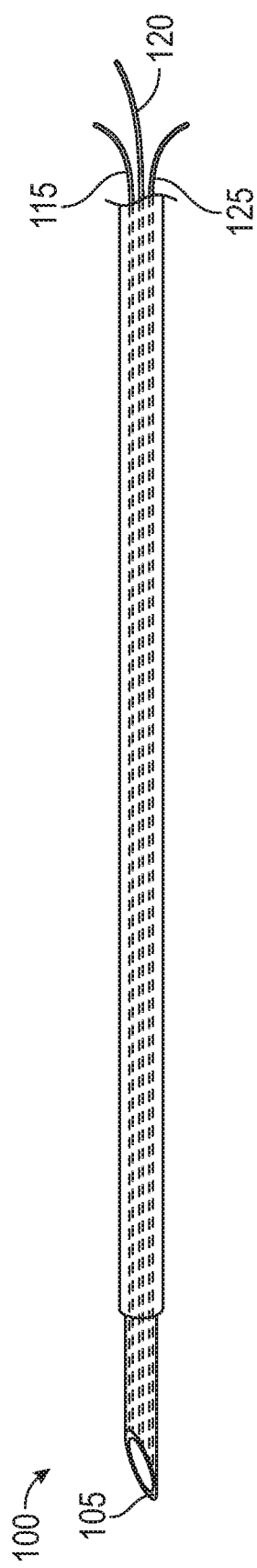
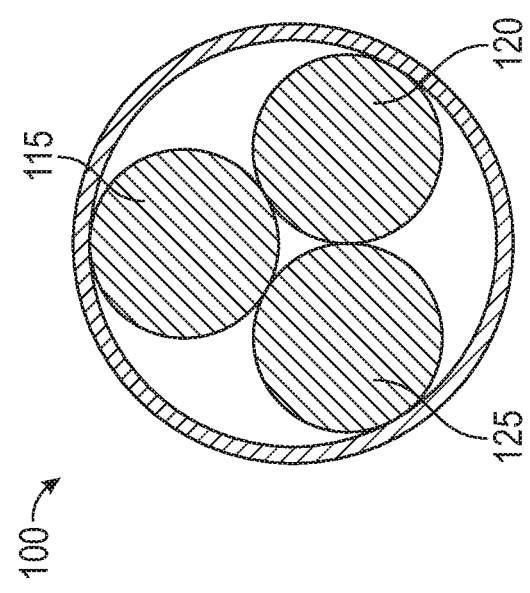
FIG. 3
FIG. 4

INTRAVENOUS THERAPY SYSTEM FOR BLOOD VESSEL DETECTION

RELATED APPLICATIONS

This application claims the benefit of U.S. Provisional Application No. 62/794,442, filed Jan. 18, 2019, and entitled SMART NEEDLE FOR PIVC INSERTION, which is incorporated herein in its entirety.

BACKGROUND

Needles may be used for a variety of infusion therapies. For example, needles may be used for infusing fluids, such as a saline solution, various medicaments, and parenteral nutrition, into a patient. Needles may also be used for withdrawing blood from the patient. To facilitate insertion into a body, the needle includes a distal tip that includes a bevel used to interface with a skin of a patient as the bevel faces away from skin of the patient. During use of the needle, the needle is inserted at a shallow angle through the skin of the patient and into a vein of the patient so as to retrieve a blood sample or introduce a medicament or a plurality of medicaments.

Needle insertion into a vein has been difficult for phlebotomists, clinicians, and other health care provider at times because veins can be hard to see or palpate. Heat problems, dehydration, and age of the patient may all be some contributors to the inability to access any given patient's blood vessels. Near infrared (NIR)-based vein finders can show superficial veins up to 4-6 mm deep within a human arm, for example. This depth within the human body, however, may not sufficient to allow a clinician to easily access any given veins. Ultrasound-based devices can identify those veins that are much deeper than 4-6 mm. However, ultrasound machines are expensive and bulky to use in all circumstances. As a consequence, clinicians may be left to insert the needle into subcutaneous layers of a patient's skin hoping to access a blood vessel. Such unassisted insertions, especially where a number of sequential insertions are attempted, may cause substantial pain, bruising, discomfort, and anxiety in patients to which the insertions are subjected to.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to vascular access devices and related systems and methods. In some embodiments, an intravenous therapy system provides for the detection of veins within a patient. The intravenous therapy system may include a hollow needle comprising a distal end and a proximal end, the distal end comprising a sharp tip for insertion into a vein. In some embodiments, an infrared (IR) camera is placed within a hollow portion of the hollow needle. In some embodiments, the IR camera includes an IR detector; a first light source to emit a first wavelength of IR light; and a second light source to emit a second wavelength of IR light. In some embodiments, a comparator may be communicatively coupled to the IR camera such that, upon execution of a processor, the comparator compares an amount of black-body radiation received at the IR detector during activation of the first light and second light and provides an indication of maximum light absorption within a vein. As such, the embodiments described herein allow for relatively easier and cheaper methods for inserting a needle into a patient's blood vessels. During operation of the intravenous therapy system, a clinician may more easily insert a needle into a patient's body limiting the damage to the patient's body in doing so while also increasing the physical and mental comfort to the patient. Because of the portable nature of the intravenous therapy system, a clinician may deploy the intravenous therapy system whenever blood is to be drawn from the patient or a medicament it to be administered to the patient.

In some embodiments, the intravenous therapy system may include an audio indicator. In some embodiments, the audio indicator may include a speaker to provide feedback to a user of the intravenous therapy system indicating an optimal insertion trajectory of the hollow needle into a body based on a detected level of light absorption by the IR detector. By providing an audio indicator, a clinician may receive input from the speaker as to the location of the needle as the clinician is inserting the needle within the patient.

In some embodiments, the intravenous therapy system may further include an arm band communicatively coupled to the comparator. In some embodiments, the arm band may include a visual indicator that includes an indicator light to provide feedback to a user of the intravenous therapy system indicating an optimal insertion trajectory of the hollow needle into a body based on a detected level of light absorption by the IR detector. With the arm band, the presently described embodiments may allow for a clinician to visually ascertain the position of the needle within the patient's body during insertion. In some embodiments, the arm band may include both the visual indicator as well as the audio indicator. In these embodiments, one of the visual or audio indicator may indicate to the clinician an x-y position of the needle within the patient's body, while the other of the audio and visual indicator may indicate to the clinician the z-position of the needle within the patient's body.

In some embodiments, the IR camera may be selectively removable from within the hollow portion of the hollow needle. In these embodiments, a clinician, during use of the intravenous therapy system, may insert the needle into a patient's body in order to direct the needle into a blood vessel of the patient. Once the vein has been accessed, the clinician may remove the IR camera from within the hollow of the needle by, for example, pulling the IR camera from a distal end of the needle. This may allow for some or additional blood flow out of the needle. In a separate embodiment, the IR camera and its components may remain within the hollow of the needle as blood is drawn from the patient or medicaments are administered to the patient through the needle of the intravenous therapy system.

In some embodiments, the first light source and second light source may each emit a distinct and different wavelength of light. In some embodiments, the first light source emits a first wavelength of IR light between 940 nm and 980 nm. In some embodiment, the second light source emits a second wavelength of IR light between 630 nm and 780 nm. In some embodiments, the IR camera may emit the first wavelength of IR light at the first light source and, upon detection of the presence of a blood vessel by the comparator, the IR camera emits the second wavelength of IR light at the second light source.

In some embodiments, the components of the IR camera may further include an IR detector that further includes a photodiode optically coupled to an optical fiber passed through the hollow of the hollow needle. This may allow for larger components of the IR camera from being put in the hollow of the needle increasing the usable space within the hollow of the needle.

In some embodiments, the components of the IR camera may include a first light source that further comprises a first light-emitting diode (LED) optically coupled to an optical fiber passed through the hollow of the hollow needle. This may allow for larger components of the IR camera from being put in the hollow of the needle increasing the usable space within the hollow of the needle.

In some embodiments, the components of the IR camera may include a second light source that further includes a second light-emitting diode (LED) optically coupled to an optical fiber passed through the hollow of the hollow needle. This may allow larger components of the IR camera to not be put in the hollow of the needle, thus increasing the usable space within the hollow of the needle.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 3 is side view of a needle including an IR camera according to some embodiments of the present disclosure;

FIG. 4 is a cross-sectional view of a needle including an IR camera according to some embodiments of the present disclosure;

DESCRIPTION OF EMBODIMENTS

Figure 1:
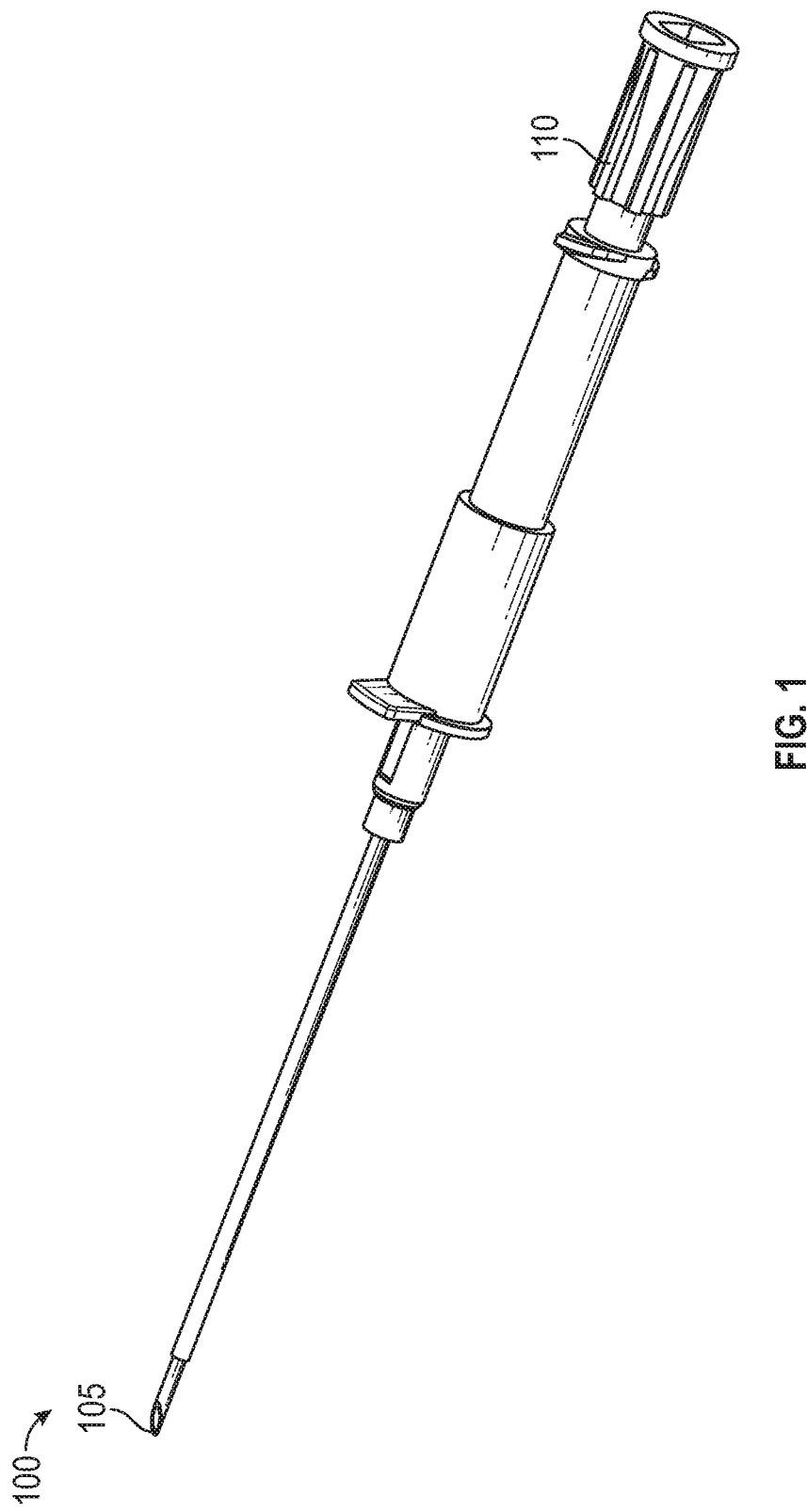
FIG. 1 is a perspective view of a needle of an intravenous therapy system according to some embodiments of the present disclosure.

As used herein, the term "proximal" refers to a location on the needle of an intravenous therapy system that, during use, is closest to the clinician using the intravenous therapy system and farthest from the patient in connection with whom the device is used. Conversely, the term "distal" refers to a location on the needle of an intravenous therapy system that, during use, is farthest from the clinician using the intravenous therapy system and closest to the patient in connection with whom the intravenous therapy system is used.

As used herein, the term "top", "up", or "upwardly" refers to a location on the needle of this intravenous therapy system that, during use, is radially away from the longitudinal axis of the intravenous therapy system and away from the patient's skin. Conversely, as used herein, the term "bottom", "down", or "downwardly" refers to a location on the needle of this intravenous therapy system that, during use, is radially away from the longitudinal axis of the device and toward the patient's skin.

As used herein, the term "in" or "inwardly" refers to a location with respect to the needle of this intravenous therapy system that, during use, is toward the inside of the intravenous therapy system. Conversely, as used herein, the term "out" or "outwardly" refers to a location with respect to the needle of this intravenous therapy system that, during use, is toward the outside of the intravenous therapy system.

This invention is described herein using like reference numbers for like elements in the different embodiments. Although the embodiments described herein are used in connection for use as an intravenous therapy system to receive a blood sample or introduce a medicament into the body of a patient, it is to be understood that this intravenous therapy system is applicable to other medical devices where it is desirable for a needle to be inserted into a blood vessel of a patient. In addition, while the embodiments of the intravenous therapy system are satisfied by embodiments in many different forms, there are shown in the drawings and herein described in detail, preferred embodiments of the invention with the scope of the disclosure measured by the appended claims.

Referring now to FIG. 1, in some embodiments, the intravenous therapy system described herein includes a needle 100. The needle 100 may be any type of needle that may be introduced into the body of a patient in order to access a patient's blood vessel or vessels. The needle 100 includes a sharp distal tip 105 defined by a bevel and a proximal end connected to a distal end of the needle hub 110. The needle 100 may be formed from stainless steel in some embodiments. Materials that can be used to form needle hub 110 include, but are not limited to, thermoplastic polymeric resins such as polycarbonate, polystyrene, polypropylene and the like. It is understood in the present disclosure, however, that other materials could be used to form needle hub 110 and needle 100.

The needle hub 110 may be formed with a funnel configuration where a smaller diameter portion of the funnel configuration is connected to a proximal end of the needle 100. This configuration may facilitate for the insertion of another medical device within the hollow of the needle 100 such as an IR camera described herein or other types of devices, such as a guidewire, into the proximal end of needle 100. In addition, a smaller portion of the funnel configuration may enhance the initial visualization of blood when blood flows out of the proximal end of needle 100 due to a faster blood flow front caused by the smaller portion of funnel configuration. In some embodiments presented herein, the IR camera may, during insertion into the hollow of the needle 100, allow for the passage of fluids such as blood or medicaments to pass through the hollow of the needle 100. In this embodiment, the components of the IR camera may fit within the hollow of the needle 100 so as to allow such passage of blood, medicaments, or both. The needle hub 110 may be fitted to communicatively couple to any of a number of connections to, for example, a fluid reservoir. The needle hub 110, in some embodiments, may include a pair of finger grips or other knurling disposed around the needle hub 110. The knurling may allow for ease of interaction by a clinician when interfacing the needle 100 with other medical devices. As such, the needle hub 110 may provide for a comfortable gripping surface for the clinician and a readily distinguishable finger placement location that keeps the clinician's fingers clear of the needle 100 or its distal tip 105.

As described herein, in some embodiments, the needle 100 may house an infrared (IR) camera within a hollow portion of the needle 100. The IR camera may include an IR detector, in some embodiments. The IR detector may be any device that detects reflected or emitted light. In an embodiment, the IR detector may detect this light through active illumination by a first light source or a second light source. In an embodiment, the light detected at the IR detector may be near infrared, mid-infrared, or far infrared. In some embodiments, the light detected may have a wavelength spectrum that extends from the nominal red edge of the visible spectrum at 700 nanometers to 1 millimeter. In an embodiment, the light detected by the IR detector may have a wavelength of between 940 nm and 980 nm. In an embodiment, the light detected by the IR detector may have a wavelength of 960 nm. In an embodiment, the light detected by the IR detector may have a wavelength of between 620 nm and 980 nm. In an embodiment, the light detected by the IR detector may have a wavelength of 660 nm.

As described herein, the light detected at the IR detector may be dependent on a light source associated with the IR camera, a mode of operation of the IR camera, or both. The present specification contemplates that the IR camera may detect any infrared light as may suit a particular application of the principles described herein, including the detection of an infrared light upon insertion of the needle 100 into a body or into a blood vessel.

The needle 100 may incorporate any number of devices that allow for the selective passage of blood or medicaments out of and into, respectively, the body. Examples of these additional devices may include vented plugs, fluidic leads, and valves, among others. The present specification, therefore, contemplates the use of these other devices coupled to or integrated into the needle 100 as may suit a particular application of the principles described herein.

In an embodiment, the IR camera housed within the hollow of the needle 100 may further include one or more light sources. In a specific embodiment, the light sources may include a first light source and a second light source. Each of the first and second light sources may be placed within the hollow of the needle 100 along with the IR detector as described herein. The first and second light sources may each emit an IR light at a specific wavelength. In a specific embodiment, the first light source may emit a first IR light at a first wavelength or range of wavelengths while the second light source emits a second IR light at a second wavelength or range of wavelengths. In some embodiments, the range of wavelengths of IR light emitted by the first IR light source may overlap with the wavelength or range of wavelengths emitted by the second IR light source. In some embodiments, the range of wavelengths of IR light emitted by the second IR light source may overlap with the wavelength or range of wavelengths emitted by the first IR light source.

In an embodiment, the IR camera may wirelessly communicate with a processor so as to provide feedback to the processor regarding detected wavelengths of IR light. In this embodiment, the IR camera may be maintained within the needle 100 as the needle is inserted and removed from the body of the patient. In some embodiments, after insertion of the needle 100 into the body of the patient, the IR camera may be used to detect the position of the needle 100 within the patient's body relative to a blood vessel such as a vein or artery. In a human body, for example, the blood vessels of the circulatory system transport blood throughout the body. The arteries are blood vessels that transport blood away from the heart while the veins transport blood to the heart. A distinguishing feature of the veins, in some examples, is the inclusion of a number of valves formed therein to prevent backflow of blood away from the heart. During use of the needle 100, certain infusing fluids, medicaments, parenteral nutrition, or other medicaments may be introduced into a vein in order to cause these medicaments to enter the blood stream at a location where they will be received by the heart and distributed throughout the body. It is, in some situations, desirable to distribute these medicaments throughout the body through the introduction of these medicaments into veins rather than allow the medicaments to be injected into other soft tissues within the body or even within an artery. Because the introduction of the medicaments into an artery may not effectively and evenly distribute these medicaments into the body, the IR camera described herein may allow for the receipt of feedback relative to whether the needle is being inserted into a vein or an artery. During use, the needle 100 may be inserted into the human body at a location where a vein is anticipated to be located. During insertion, the IR camera may emit an IR light from one or both of the first IR light source and second IR light source. Any reflected IR light may be reflected back to the IR detector of the IR camera, captured, and analyzed for signal strength (i.e., intensity, wavelength, frequency, among other factors). When the distal tip 105 of the needle 100 is pointed towards a blood vessel, the signal strength from the reflected IR light may indicate the type of blood vessel in front of the IR camera. In a specific embodiment, the signal strength received at the IR camera may be weaker where the absorption of the IR light by the blood is higher. In some examples, the relative levels of absorbed/reflected light detected at the IR camera may indicate whether the blood vessel is a vein or artery due to the level of oxygen present in the blood maintained in these types of blood vessels. Oxygenated blood within an artery, for example, absorbs more IR light than deoxygenated blood within a vein at wave length greater than 800 nm. This absorption behavior is reversed for wavelengths less than 800 nm. In an embodiment, the differences in light reflection at one or more different wavelengths may indicate the position of the needle 100 relative to a vein or an artery.

As described herein, an IR camera that includes an IR detector and two distinct IR wavelength or near-IR wavelength emitting diodes may be used to initially scan an area of interest along a patient's body at a near-IR wavelength (e.g., 960 nm) in order to detect a region of low reflected light related to a high absorption of that light indicating the presence of a blood vessel. The IR camera may then switch to emitting a different wavelength of IR light (e.g., 650 to 760 nm). In this embodiment, when the absorption coefficient is increased, the blood vessel detected is a vein. Where the absorption coefficient is decreased, the blood vessel is an artery.

In an embodiment, an initial scan of a scan an area of interest along a patient's body may be done with emitting a wavelength between 650 nm or 760 nm. In this embodiment, the second scan is done with a diode emitting a wavelength of IR light a 960 nm. In this specific embodiment, a detected increase in absorption coefficient would indicate an artery while a detected decrease in absorption coefficient would indicate a vein.

In some embodiments described herein, any initial scan of an area of interest along a patient's body may be conducted before penetrating the patient's skin with the needle 100. This may be done where a clinician or other health care provider (HCP) visually detects a superficial vein at the area of interest. If the clinician or other HCP cannot visually detect a vein, the scan can be done after the needle 100 has penetrated the patient's skin. Accordingly, the present specification describes a vein and artery detection device that may be used above the patient's skin as well as within the patient's body.

In an embodiment, the orientation of the needle and the IR camera or near-IR camera therein provides a two-dimensional image of the veins and/or arteries in front of the needle. Where the detected blood vessel is not centered in the image, the needle orientation is to be adjusted. Other types of visual, audio, and haptic indicators may be used to indicate the location and presence of the blood vessel being accessed.

Figure 2:
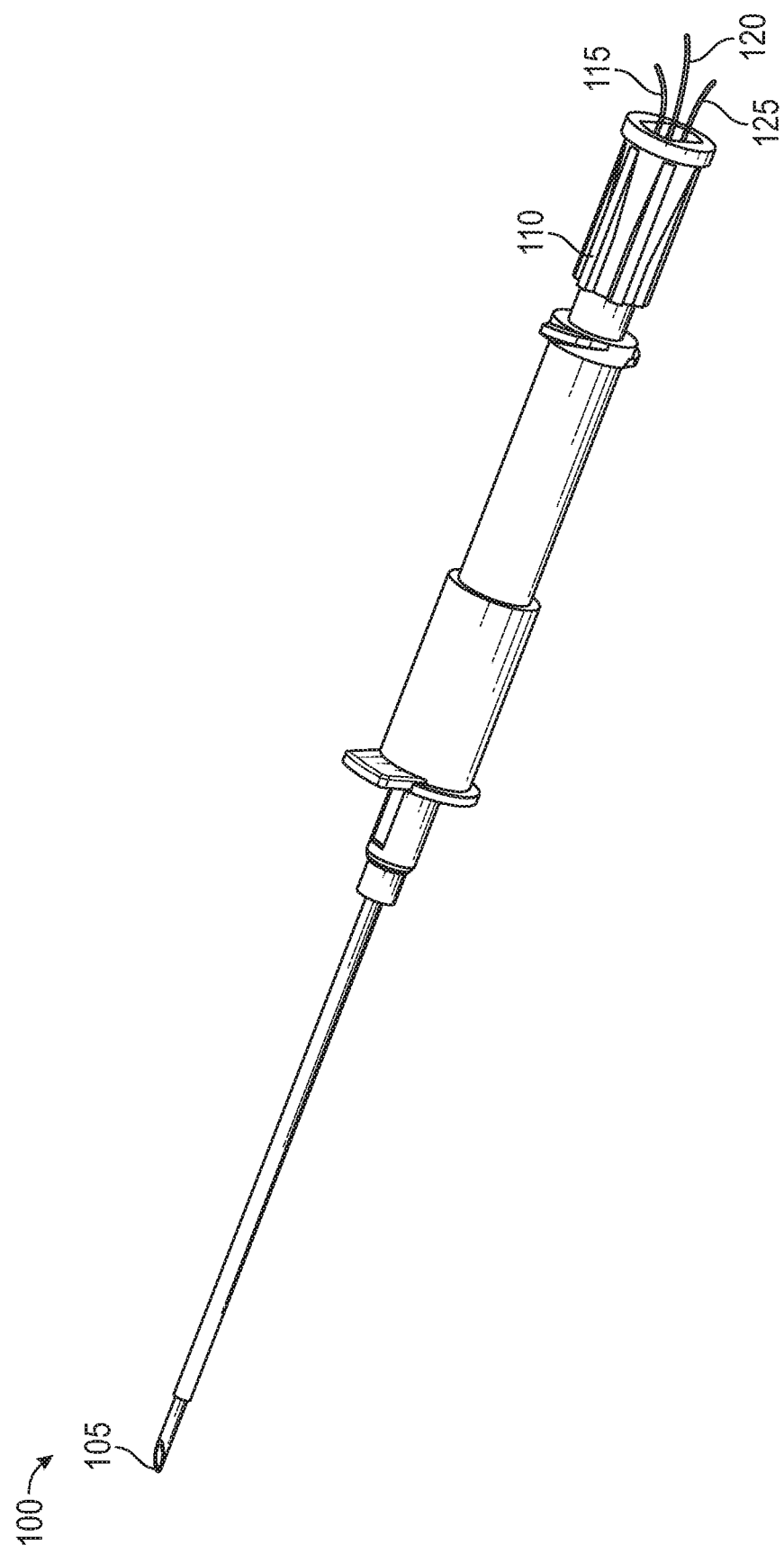
FIG. 2 is a perspective view of a needle of an intravenous therapy system according to some embodiments of the present disclosure.

FIG. 2 is a perspective view of a needle 100 of an intravenous therapy system according to some embodiments of the present disclosure. In some embodiments, such as presented in FIG. 2, the needle 100 may have a number of leads 115, 120, 125. In the embodiment shown in FIG. 2, the leads 115, 120, 125 may include an IR detector lead 115, a first light source lead 120, and a second light source lead 125. In an embodiment, the IR detector may include the IR detector lead 115. In an embodiment, the first light source may include the first light source lead 120. In an embodiment, the second light source may include the second light source lead 125.

In an embodiment, the components of the IR camera formed within the hollow of the needle (i.e., the IR detector, the first IR light source, and the second IR light source) may be removed upon insertion of the needle 100 within the patient and access of the needle 100 with a vein in the patient's body. In this embodiment, the IR detector lead 115 may be a draw wire that is physically coupled to the IR detector in order to allow a clinician to selectively remove the IR detector from within the hollow of the needle 100 via the proximal end of the needle 100 after insertion of the needle 100 and access to a vein. Additionally, in an embodiment, the first light source lead 120 may be a draw wire that is physically coupled to the first light source in order to allow a clinician to selectively remove the first light source from within the hollow of the needle 100 via the proximal end of the needle 100 after insertion of the needle 100 and access to a vein. Additionally, in an embodiment, the second light source lead 125 may be a draw wire that is physically coupled to the second light source in order to allow a clinician to selectively remove the second light source from within the hollow of the needle 100 via the proximal end of the needle 100 after insertion of the needle 100 and access to a vein. In these embodiments, the IR detector, first light source, and second light source may be removed by a clinician by pulling the IR detector lead 115, first light source lead 120, and second light source lead 125, individually or together, from the opening of the proximal end of the needle 100. In these embodiments, the removal of the IR detector, first light source and second light source may allow a fluid, such as blood or a medicament, to pass through the hollow of the needle. In this specific example, the IR detector, first light source, and second light source include their own electrical source incorporated therein so as to operate according to the methods of operation described herein.

In an embodiment, the IR detector lead 115, the first light source lead 120, and the second light source lead 125 may each be an electrical and communicative connection to the IR detector, the first light source, and the second light source, respectively. In an embodiment, the IR detector lead 115 may supply power to the IR detector as well as allow the IR detector to communicate data received at the IR detector to, for example, a processor of an information handling system. Similarly, the first light source lead 120 and second light source lead 125 may be electrically coupled to the first light source and second light source, respectively, in order to selectively receive an electrical current at a voltage in order to cause the light sources to illuminate. In each of these embodiments, the IR detector lead 115, first light source lead 120, and second light source lead 125 may be coupled to the IR detector, the first light source, and the second light source, respectively, such that pulling on the leads 115, 120, 125 allows the clinician to remove the IR detector, the first light source, and the second light source from within the hollow of the needle 100 via the proximal end of the needle 100 as described herein. In any embodiment described herein, the IR detector, the first light source, and the second light source may be sized within the hollow of the needle 100 such that despite the presence of the IR detector, the first light source, and the second light source, fluids such as blood or medicaments may pass through the hollow of the needle 100.

In an embodiment, the IR detector lead 115, the first light source lead 120, and the second light source lead 125 may each be a strand of optical fiber. In this embodiment, the optical fiber leads 115, 120, 125 may each provide an optical path for light to pass along the optical fiber and to their respective elements. By way of example, a terminal end of the IR detector lead 115 may be coupled to an IR detector such that light received at a distal end of the optical fiber coupled to the IR detector within the hollow of the needle 100 allows the IR detector to detect light from within the body of the patient during insertion of the needle 100 into the patient's body. In an embodiment, a terminal end of the first light source optical cable 120 may be coupled to the first light source. During insertion of the needle 100 or while the needle 100 is within the patient's body, the light emitted from the first light source may travel down the first light source optical fiber 120 and illuminate the areas within the body for the IR detector to detect. In an embodiment, a terminal end of the second light source optical cable 125 may be coupled to the second light source. During insertion of the needle 100 or while the needle 100 is within the patient's body, the light emitted from the second light source may travel down the second light source optical fiber 125 and illuminate the areas within the body for the IR detector to detect.

Each of the embodiments described herein with regards to the leads 115, 120, 125 used in connection with the IR detector, the first light source, and second light source may be used to detect the presence or absence of a vein within the human body. According to an embodiment, the needle 100 with the IR camera therein may be used to detect a patient's blood vessels from without the patient's body. According to another embodiment, the needle 100 may be used to detect a patient's blood vessels from within the patient's body. During operation and via comparison of the detected IR light reflected off of the objects within the body, the clinician may also detect whether a blood vessel is an artery or a vein based on the amount of oxygen present in the blood to absorb or not absorb the IR light emitted from either the first or second light source.

During operation of the needle 100, the IR camera may initially scan an area of interest along a patient's body at a near-IR wavelength (e.g., 960 nm) with a first diode in order to detect a region of low reflected light related to a high absorption of that light indicating the presence of a blood vessel. The IR camera may then switch to emitting a different wavelength of IR light (e.g., 650 to 760 nm) with a second diode. In this embodiment, when the absorption coefficient is increased, the blood vessel detected is a vein. Where the absorption coefficient is decreased, the blood vessel is an artery.

In an embodiment, an initial scan of a scan an area of interest along a patient's body may be done with emitting a wavelength between 650 nm or 760 nm. In this embodiment, the second scan is done with a diode emitting a wavelength of IR light a 960 nm. In this specific embodiment, a detected increase in absorption coefficient would indicate an artery while a detected decrease in absorption coefficient would indicate a vein.

In some embodiments described herein, any initial scan of an area of interest along a patient's body may be conducted before penetrating the patient's skin with the needle 100 as described herein. This may be done when a clinician or other health care provider (HCP) visually detects a superficial vein at the area of interest. If the clinician or other HCP cannot visually detect a vein, the scan can be done after the needle 100 described herein has penetrated the patient's skin. Accordingly, the present specification describes a vein and artery detection device that may be used in both above the patient's skin as well as within the patient's body.

In an embodiment, the orientation of the needle and the IR camera or near-IR camera therein provides a two-dimensional image of the veins and/or arteries in front of the needle. Where the detected blood vessel is not centered in the image, the needle orientation is to be adjusted. Other types of visual, audio, and haptic indicators may be used to indicate the location and presence of the blood vessel being accessed.

FIG. 3 is side view of a needle 100 including an IR camera according to some embodiments of the present disclosure. FIG. 4 is a cross-sectional view of a needle 100 including an IR camera according to some embodiments of the present disclosure. In each of these figures, the IR detector lead 115, first light source lead 120, and second light source lead 125 are shown within the hollow of the needle 100. Although in these embodiments shown in FIGS. 3 and 4 do not show the IR camera, the first light source, and the second light source specifically, the size of the components of the IR camera may be as small or smaller than their respective leads 115, 120, 125 and may be fixed to the distal ends of each of the leads 115, 120, 125. In another embodiment, the leads 115, 120, 125 may be optical fibers that optically couple the IR detector, the first light source, and the second light source to the distal ends of their respective leads 115, 120, 125.

FIG. 4 shows an embodiment where the leads 115, 120, 125 and/or components of the IR camera fit within the hollow of the needle 100. Although FIG. 4 shows that the leads 115, 120, 125 or components of the IR camera are of equal size, some or all of the cross-sectional diameters or dimensions of the IR detector, first light source, second light source or any associated leads 115, 120, 125 may be larger or smaller than depicted in FIG. 4. In the embodiment shown in FIG. 4, the three leads 115, 120, 125 or components of the IR camera are compacted within the hollow of the needle 100 with some spaces in between. This empty space may be filled with blood or a medicament upon insertion of the needle 100 into the patient's body. In other examples, the leads 115, 120, 125 or components of the IR camera may be packed into the hollow of the needle 100 so as to not have any gaps or spaces present between the leads 115, 120, 125 or components. In this embodiment, the leads 115, 120, 125 or the leads 115, 120, 125 and coupled components may be pulled out from within the hollow of the needle 100 after insertion and access of a vein by the needle 100.

Figure 5:
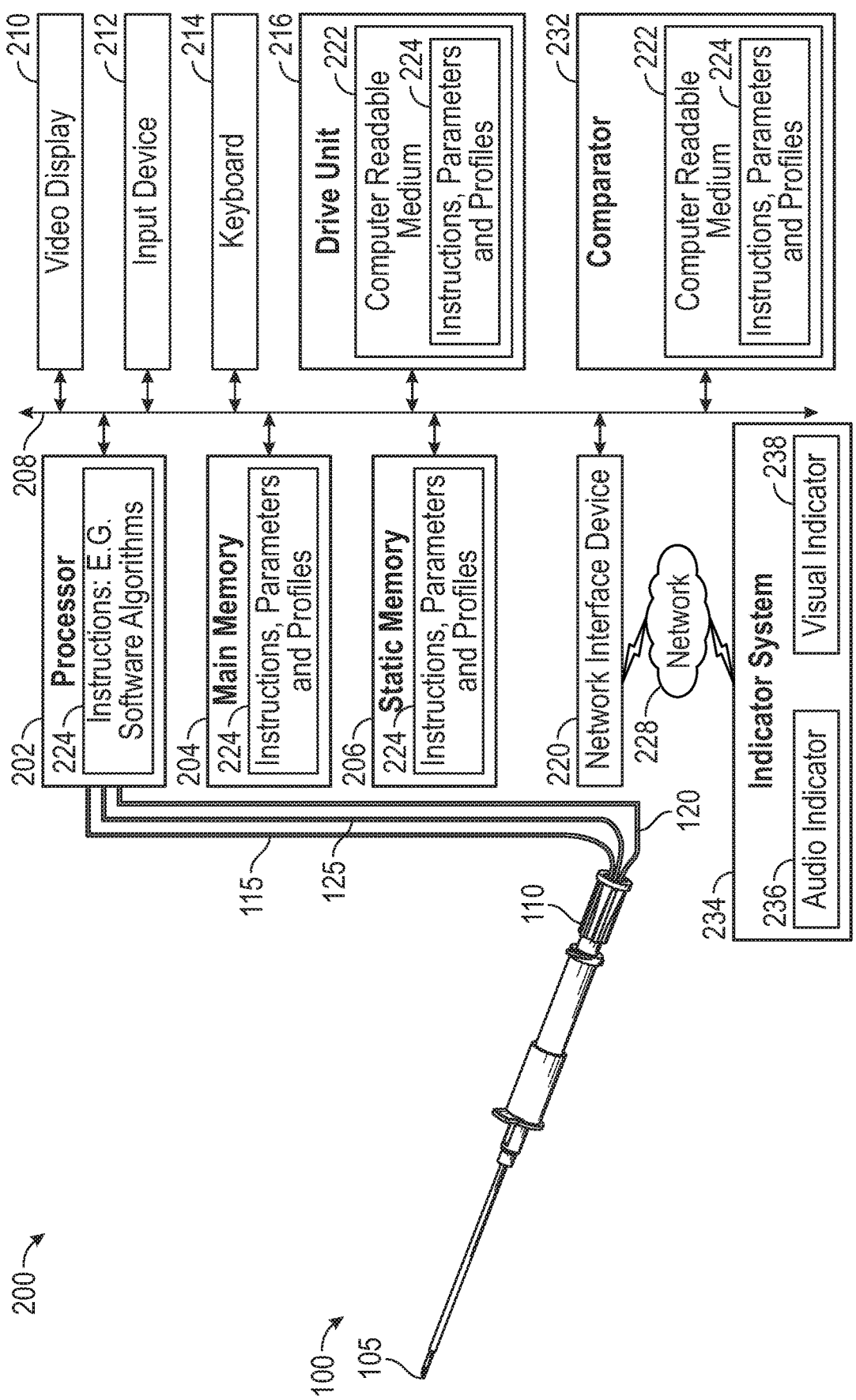
FIG. 5 is a block diagram of an intravenous therapy system according to an embodiment of the present disclosure.

FIG. 5 is a block diagram of an intravenous therapy system 200 according to an embodiment of the present disclosure. In the embodiments described herein, an information handling system 200 includes any instrumentality or aggregate of instrumentalities operable to compute, classify, process, transmit, receive, retrieve, originate, switch, store, display, manifest, detect, record, reproduce, handle, or use any form of information, intelligence, or data for business, scientific, control, entertainment, or other purposes. For example, an information handling system 200 can be a personal computer, mobile device (e.g., personal digital assistant (PDA) or smart phone), server (e.g., blade server or rack server), a consumer electronic device, a network server or storage device, a network router, switch, or bridge, wireless router, or other network communication device, a network connected device (cellular telephone, tablet device, etc.), IoT computing device, wearable computing device, a set-top box (STB), a mobile information handling system, a palmtop computer, a laptop computer, a desktop computer, a communications device, an access point (AP), a base station transceiver, a wireless telephone, a land-line telephone, a control system, a camera, a scanner, a facsimile machine, a printer, a pager, a personal trusted device, a web appliance, or any other suitable machine capable of executing a set of instructions (sequential or otherwise) that specify actions to be taken by that machine, and can vary in size, shape, performance, price, and functionality.

In a networked deployment, the information handling system 200 may operate in the capacity of a server or as a client computer in a server-client network environment, or as a peer computer system in a peer-to-peer (or distributed) network environment. In a particular embodiment, the information handling system 200 can be implemented using electronic devices that provide voice, video or data communication. For example, an information handling system 200 may be any mobile or other computing device capable of executing a set of instructions (sequential or otherwise) that specify actions to be taken by that machine. Further, while a single information handling system 200 is illustrated, the term "system" shall also be taken to include any collection of systems or sub-systems that individually or jointly execute a set, or multiple sets, of instructions to perform one or more computer functions.

The information handling system can include memory (volatile (e.g. random-access memory, etc.), nonvolatile (read-only memory, flash memory etc.) or any combination thereof), one or more processing resources, such as a central processing unit (CPU), a graphics processing unit (GPU), hardware or software control logic, or any combination thereof. Additional components of the information handling system 200 can include one or more storage devices, one or more communications ports for communicating with external devices, as well as, various input and output (I/O) devices, such as a keyboard, a mouse, a video/graphic display, or any combination thereof. The information handling system 200 can also include one or more buses operable to transmit communications between the various hardware components. Portions of an information handling system 100 may themselves be considered information handling systems 200.

Information handling system 100 can include devices or modules that embody one or more of the devices or execute instructions for the one or more systems and modules described herein, and operates to perform one or more of the methods described herein. The information handling system 200 may execute code instructions 224 that may operate on servers or systems, remote data centers, or on-box in individual client information handling systems according to various embodiments herein. In some embodiments, it is understood any or all portions of code instructions 224 may operate on a plurality of information handling systems 200.

The information handling system 200 may include a processor 202 such as a central processing unit (CPU), control logic or some combination of the same. Any of the processing resources may operate to execute code that is either firmware or software code. Moreover, the information handling system 200 can include memory such as main memory 204, static memory 206, computer readable medium 222 storing instructions 224 of the comparator 232, and drive unit 216 (volatile (e.g. random-access memory, etc.), nonvolatile (read-only memory, flash memory etc.) or any combination thereof). The information handling system 200 can also include one or more buses 208 operable to transmit communications between the various hardware components such as any combination of various input and output (I/O) devices.

The information handling system 200 may further include a video display 210. The video display 210 in an embodiment may function as a liquid crystal display (LCD), an organic light emitting diode (OLED), a flat panel display, a solid-state display, or a cathode ray tube (CRT). Additionally, the information handling system 200 may include an input device 212, such as a cursor control device (e.g., mouse, touchpad, or gesture or touch screen input, and a keyboard 214.

The network interface device that may be shown as wireless adapter 220 can provide connectivity to a network 228, e.g., a wide area network (WAN), a local area network (LAN), wireless local area network (WLAN), a wireless personal area network (WPAN), a wireless wide area network (WWAN), or other networks. Connectivity may be via wired or wireless connection. The wireless adapter 220 may operate in accordance with any wireless data communication standards. To communicate with a wireless local area network, standards including IEEE 802.11 WLAN standards, IEEE 802.15 WPAN standards, WWAN such as 3GPP or 3GPP2, or similar wireless standards may be used. In some aspects of the present disclosure, one wireless adapter 220 may operate two or more wireless links. In the embodiments described herein, the network interface device 220 may wirelessly couple the information handling system 200 with an indicator system 234. In the embodiments described herein, the indicator system 234 may receive data descriptive of a position of a needle 100 within the body of a patient and the information handling system 200 may relay that positional data to the indicator system 234.

In some embodiments, software, firmware, dedicated hardware implementations such as application specific integrated circuits, programmable logic arrays and other hardware devices can be constructed to implement one or more of some systems and methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by firmware or software programs executable by a controller or a processor system. Further, in an exemplary, non-limited embodiment, implementations can include distributed processing, component/object distributed processing, and parallel processing. Alternatively, virtual computer system processing can be constructed to implement one or more of the methods or functionalities as described herein.

The present disclosure contemplates a computer-readable medium that includes instructions, parameters, and profiles 224 or receives and executes instructions, parameters, and profiles 224 responsive to a propagated signal, so that a device connected to a network 228 can communicate voice, video or data over the network 228. Further, the instructions 224 may be transmitted or received over the network 228 via the network interface device or wireless adapter 220.

The information handling system 200 can include a set of instructions 224 that can be executed to cause the computer system to perform any one or more of the methods or computer-based functions disclosed herein. For example, instructions 224 may execute a comparator 232, software agents, or other aspects or components. Various software modules comprising application instructions 224 may be coordinated by an operating system (OS), and/or via an application programming interface (API). An example operating system may include Windows®, Android®, and other OS types. Example APIs may include Win 32, Core Java API, or Android APIs.

The disk drive unit 216 and the comparator 232 may include a computer-readable medium 222 in which one or more sets of instructions 224 such as software can be embedded. Similarly, main memory 204 and static memory 206 may also contain a computer-readable medium for storage of one or more sets of instructions, parameters, or profiles 224. The disk drive unit 216 and static memory 206 may also contain space for data storage. Further, the instructions 224 may embody one or more of the methods or logic as described herein. For example, instructions relating to the comparison of IR light received at an IR detector by the comparator 232 software algorithms, processes, and/or methods may be stored here. In a particular embodiment, the instructions, parameters, and profiles 224 may reside completely, or at least partially, within the main memory 204, the static memory 206, and/or within the disk drive 216 during execution by the processor 202 of information handling system 200. As explained, some or all of the comparator 232 may be executed locally or remotely. The main memory 204 and the processor 202 also may include computer-readable media.

Main memory 204 may contain computer-readable medium (not shown), such as RAM in an example embodiment. An example of main memory 204 includes random access memory (RAM) such as static RAM (SRAM), dynamic RAM (DRAM), non-volatile RAM (NV-RAM), or the like, read only memory (ROM), another type of memory, or a combination thereof. Static memory 206 may contain computer-readable medium (not shown), such as NOR or NAND flash memory in some example embodiments. The comparator 232 may be stored in static memory 206, or the drive unit 216 on a computer-readable medium 222 such as a flash memory or magnetic disk in an example embodiment. While the computer-readable medium is shown to be a single medium, the term "computer-readable medium" includes a single-medium or multiple medium, such as a centralized or distributed database, and/or associated caches and servers that store one or more sets of instructions. The term "computer-readable medium" shall also include any medium that is capable of storing, encoding, or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random-access memory or other volatile re-writable memory. Additionally, the computer-readable medium can include a magneto-optical or optical medium, such as a disk or tapes or other storage device to store information received via carrier wave signals such as a signal communicated over a transmission medium. Furthermore, a computer readable medium can store information received from distributed network resources such as from a cloud-based environment. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

The information handling system 200 may also include the comparator 232 that may be operably connected to the bus 208. The comparator 232 computer readable medium 222 may also contain space for data storage. The comparator 232 may, according to the present description, perform tasks related to receiving input descriptive of IR light detected at an IR detector housed within the hollow of the needle 100 and compare that detected IR light with previously detected levels of IR light or a look up table.

In an embodiment, the comparator 232 may communicate with the main memory 204, the processor 202, the video display 210, the input device 212, and the network interface device 220 via bus 208, and several forms of communication may be used, including ACPI, SMBus, a 24 MHZ BFSK-coded transmission channel, or shared memory. Keyboard driver software, firmware, controllers and the like may communicate with applications on the information handling system 200.

In other embodiments, dedicated hardware implementations such as application specific integrated circuits, programmable logic arrays and other hardware devices can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

When referred to as a "system", a "device," a "module," a "controller," or the like, the embodiments described herein can be configured as hardware. For example, a portion of an information handling system device may be hardware such as, for example, an integrated circuit (such as an Application Specific Integrated Circuit (ASIC), a Field Programmable Gate Array (FPGA), a structured ASIC, or a device embedded on a larger chip), a card (such as a Peripheral Component Interface (PCI) card, a PCI-express card, a Personal Computer Memory Card International Association (PCM-CIA) card, or other such expansion card), or a system (such as a motherboard, a system-on-a-chip (SoC), or a stand-alone device). The system, device, controller, or module can include software, including firmware embedded at a device, such as an Intel® Core class processor, ARM® brand processors, Qualcomm® Snapdragon processors, or other processors and chipsets, or other such device, or software capable of operating a relevant environment of the information handling system. The system, device, controller, or module can also include a combination of the foregoing examples of hardware or software. In an embodiment an information handling system 100 may include an integrated circuit or a board-level product having portions thereof that can also be any combination of hardware and software. Devices, modules, resources, controllers, or programs that are in communication with one another need not be in continuous communication with each other, unless expressly specified otherwise. In addition, devices, modules, resources, controllers, or programs that are in communication with one another can communicate directly or indirectly through one or more intermediaries.

During operation of the information handling system 200, data may be received at the processor 202 from an IR camera within the hollow of the needle 100. As described herein the hollow of the needle 100 may house the components of the IR camera including an IR detector, a first light source that emits a first IR light, and a second light source that emits a second IR light. These components of the IR camera may be housed within the hollow of the needle 100 close to a distal tip 105 of the needle 100 so as to illuminate and detect light within the body of a patient.

In an embodiment, the processor 202 of the information handling system 200 may be communicatively coupled to the IR detector, the first light source, and the second light source by a number of leads 115, 120, 125. In this embodiment, the processor may be electrically and communicatively coupled to the IR detector by an IR detector lead 115. The IR detector lead 115 may provide power to the IR detector to operate the IR detector. Additionally, the IR detector lead 115 may include a data transmission line that receives data descriptive of light signal strengths as the needle is passed through portions of a patient's body and into a blood vessel.

The first light source lead 120 may be communicatively coupled to the processor 202 via a power source. The power source may provide a current at a certain voltage to the first light source via the first light source lead 120 so as to cause the first light source to emit light an IR light with a wavelength ranging from between 940 nm and 980 nm. In an embodiment, the first light source may emit an IR light with a wavelength of 960 nm.

The second light source lead 125 may be communicatively coupled to the processor 202 via a power source. The power source may provide a current at a certain voltage to the second light source via the second light source lead 125 so as to cause the second light source to emit an IR light having a wavelength ranging from between 630 nm and 780 nm. In an embodiment, the second light source may emit an IR light with a wavelength of 660 nm.

Continuing with the operation of the information handling system 200, the processor 202 may provide the data provided from the IR detector via the IR detector lead 115 to a comparator 232. The comparator 232 may receive the data and compare signal strength of the light received at the IR detector based on one or both of a prior detection of light at the IR detector. This data may be indicative of a specific light absorption or reflection coefficient. In an embodiment, any relative levels of any reflected light received at the IR camera from within the patient's body may indicate the presence of a blood vessel and whether the blood vessel is a vein or an artery. The determination that the reflected light indicates the presence of a blood vessel and whether the blood vessel is a vein or artery may be based on the data provided by a look-up table maintained on the computer readable medium 222 and relative levels of reflected light during insertion of the needle 100.

In an embodiment, the needle 100 may be inserted into the human body at a location where a vein is anticipated to be located or where, in an embodiment, an initial detection of a blood vessel has been indicated through use of the IR camera. During insertion, the IR camera may emit an IR light from one or both of the first IR light source and second IR light source. Any reflected IR light may be reflected back to the IR detector of the IR camera, captured by the IR detector, and analyzed by the comparator 232 for signal strength (i.e., intensity, wavelength, frequency, among other factors) in order to determine an absorption coefficient or reflection coefficient of the emitted light. When the distal tip 105 of the needle 100 is pointed towards a blood vessel, the signal strength from the reflected IR light may indicate the type of blood vessel in front of the IR camera. In a specific embodiment, the signal strength received at the IR camera may be weaker where the absorption of the IR light by the blood is higher.

Certain data descriptive of anticipated signal strengths may be maintained on the computer readable memory 222 and accessed by the comparator 232 in order to calculate an absorption coefficient or reflection coefficient of the emitted light and determine whether a blood vessel is present in front of the IR detector and whether the blood vessel, where present, is a vein or artery. In some examples, the relative levels of absorbed/reflected light detected at the IR camera (i.e., the signal strength detected by the IR detector) may further indicate whether the blood vessel is a vein or artery due to the level of oxygen present in the blood maintained in these types of blood vessels. Specifically, where oxygen-rich blood is present in an artery, IR light may be absorbed more readily at certain IR wavelengths (i.e., 960 nm). Conversely, where deoxygenated blood is present in a vein, IR light may not be absorbed at a specific wavelength (e.g., 800 nm) as readily allowing for relatively more IR light to be reflected back to the IR detector in the IR camera.

In an embodiment, the differences in light reflection at one or more different wavelengths may indicate the position of the needle 100 relative to a vein or an artery. The comparator 232 may make these determinations as to higher signal strength at the IR detector and cause output to a video display 210, an audio output device, the audio indicator 236 of the indicator system 234, or a visual indicator 238 of the indicator system 234 to help direct a clinician or other HCP to orient the needle 100 within the body of the patient.

In an embodiment, the indicator system 234 may be communicatively coupled to the information handling system 200 via either a wired or, as shown in FIG. 5, a wireless connection. Where the indicator system 234 is communicatively coupled to the information handling system 200 via a wired connection, the information handling system 200 may further provide power to the indicator system 234 along with data descriptive of how to direct a clinician to direct or move a needle within a patient's body.

In an embodiment, the indicator system 234 may be a pad that is coupled to a portion of a patient's body so that a clinician can receive real-time input from the indicator system 234 and based on the data from the comparator 232 while inserting the needle 100 into the patient's body and while orienting the needle 100 within the patient's body. The indicator system 234 may be oriented on the patient's body so as to be within the visual peripheral of the clinician to direct the clinician as described.

Figure 6A:
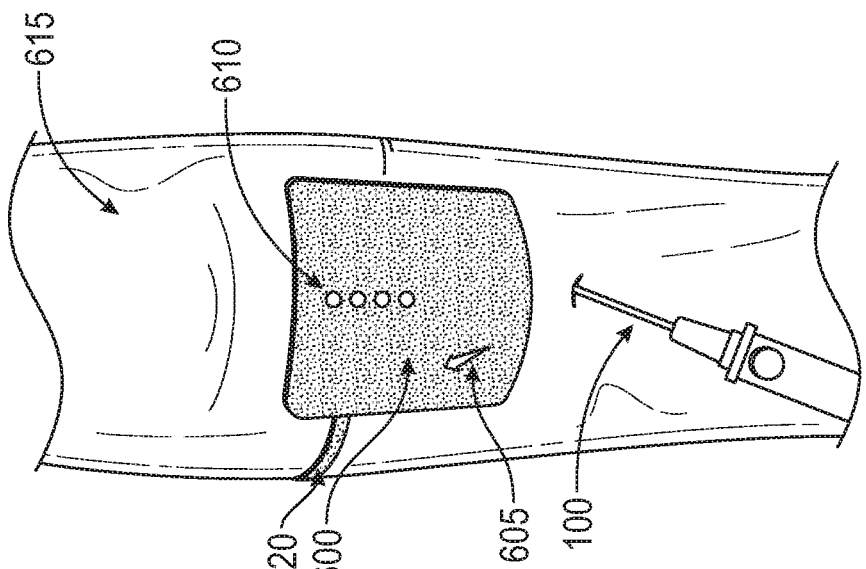
FIG. 6A is top view of a needle of an intravenous therapy system inserted into an arm of a patient according to some embodiments of the present disclosure.
Figure 6B:
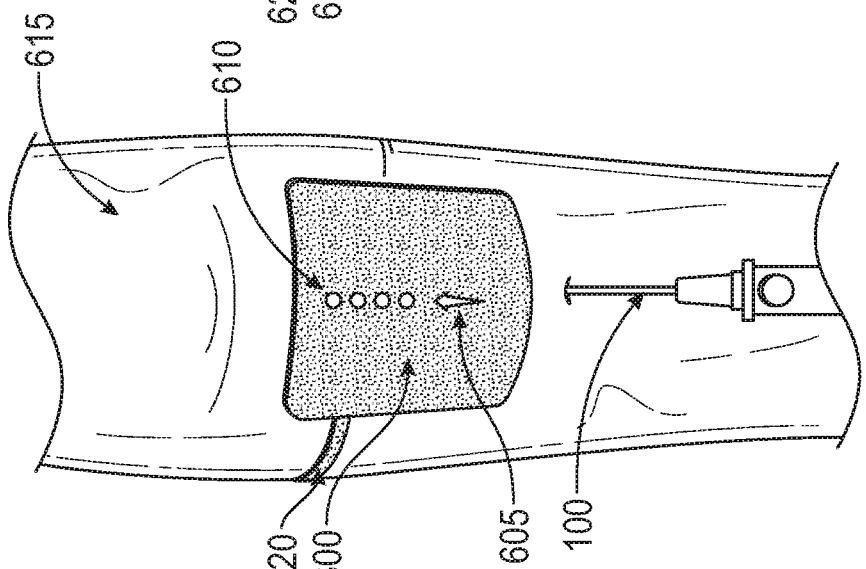
FIG. 6B is top view of a needle of an intravenous therapy system inserted into an arm of a patient according to some embodiments of the present disclosure.
Figure 6C:
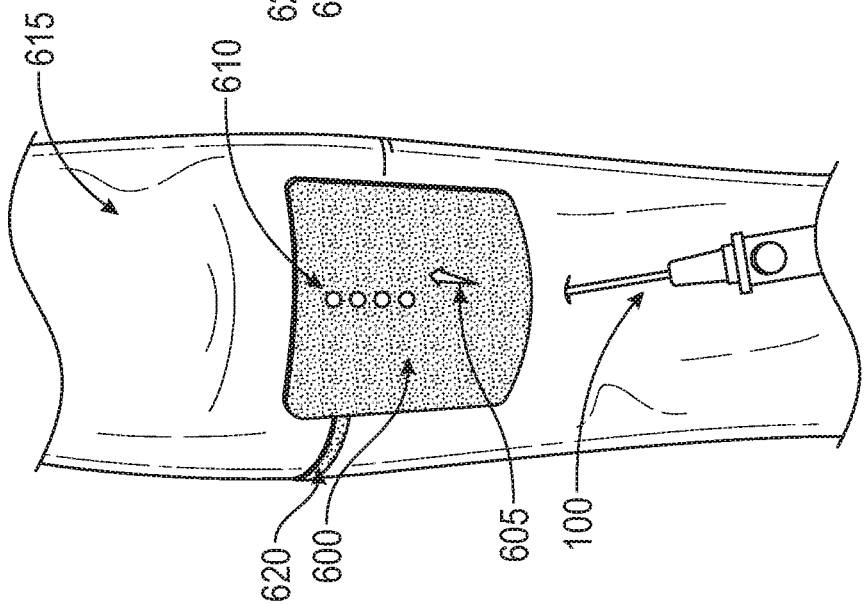
FIG. 6C is top view of a needle of an intravenous therapy system inserted into an arm of a patient according to some embodiments of the present disclosure.

FIG. 6A is top view of a needle of an intravenous therapy system inserted into an arm 615 of a patient according to some embodiments of the present disclosure. FIG. 6B is top view of a needle of an intravenous therapy system inserted into an arm 615 of a patient according to some embodiments of the present disclosure. FIG. 6C is top view of a needle of an intravenous therapy system inserted into an arm 615 of a patient according to some embodiments of the present disclosure. Each of FIGS. 6A, 6B, and 6C show a needle 100 inserted into an arm 615 of a patient. Additionally, each of FIGS. 6A, 6B, and 6C show an indicator system 600 similar to the indicator system described in connection with FIG. 5.

During operation of the indicator system 600, a clinician may insert the needle 100 into, in this example, the arm 615 of a patient. The patient's arm 615 may include a plurality of locations where a blood vessel may be located. As described herein, the needle 100 may include an IR camera that includes, in an embodiment, an IR detector, a first light source, and a second light source placed within the hollow of the needle 100. These components of the IR camera may be communicatively and operatively coupled to a processor of, for example an information handling system. The first and second light sources in this embodiment may be controlled by the processor of the information handling system while the IR detector is communicatively coupled to the processor so as to provide light signal strength data from the IR detector.

Before or as the clinician inserts the needle 100 into the patient's body, the first light source may be activated initially so as to scan an area of interest along a patient's body at a near-IR wavelength (e.g., 960 nm) in order to detect a region of low reflected light related to a high absorption of that light indicating the presence of a blood vessel. In an embodiment, the light emitted by the first light source may have a wavelength of between 940 nm and 980 nm. In an embodiment, the light emitted by the first light source may have a wavelength of 940 nm. The emission of the light from the first light source may reflect off of internal portions of the patient's body and be received at the IR detector of the IR camera. The reflected light detected at the IR detector as the needle 100 is initially inserted into the patient's body may be used as a benchmark indicating an anticipated detected light signal strength as the IR detector detects light reflected from a blood vessel.

In an embodiment, the indicator system 600 may include a number of visual indicators 605, 610 that help direct the clinician as to how to insert and orient the needle 100 into the patient's body. Any number and types of visual indicators may be used. In the embodiment presented in FIGS. 6A, 6B, and 6C, the visual indicators 605, 610 may include an arrow indicator 605 and an LED indicator 610. In this specific embodiment, the arrow indicator 605 may provide feedback to the clinician as to how to orient the needle 100 within the patient's body along an x-y plane; the x-y plane laying parallel to the surface of the patient's body (i.e., in this embodiment, the surface of the patient's arm 615). In this specific embodiment, the LED indicator 610 may provide feedback to the clinician as to how to orient the needle 100 within the patient's body along a z-axis. The z-axis may define a depth within the patient's body. In this embodiment, the LED indicator 610 may increase the number of LEDs of the LED indicator 610 to indicate how shallow or how deep to orient the needle 100 within the patient's arm 615.

In an embodiment, as the light signal strength detected by the IR detector changes to indicate the presence of a blood vessel, the first light source may be turned off and a second light source may be turned on. In an embodiment, the second light source may emit IR light having a wavelength between 630 nm and 780 nm. In an embodiment, the second light source may emit an IR light have a wavelength of 660 nm.

In embodiment, and as the first light source is turned off and the second light is turned on, the indicator system 600 may direct the clinician as to how to orient the needle 100 within the patient's body to access a vein with the needle 100. In an embodiment, when the first light source is turned off and the second light source is turned on, the information handling system may indicate to the comparator that a comparison between different signal strengths is being conducted in order to distinguish between an artery and a vein as described herein. This allows the comparator to refer to a look-up table to determine which detected signal strengths indicate the presence of an artery or a vein.

In a human body, for example, the blood vessels of the circulatory system transport blood throughout the body. The arteries are blood vessels that transport blood away from the heart while the veins transport blood to the heart. A distinguishing feature of the vein may include the presence of a number of valves formed therein to prevent backflow of blood away from the heart. Additionally, veins are those blood vessels that direct the blood back to the heart. During use of the needle 100, certain infusing fluids, parenteral nutrition, or other medicaments may be introduced into a vein in order to cause these medicaments to enter the blood stream at a location where they will be received by the heart and distributed throughout the body. It is, in some situations, desirable to distribute these medicaments throughout the body through the introduction of these medicaments into veins rather than allow the medicaments to be injected into other soft tissues within the body or even within an artery. Because the introduction of the medicaments into an artery may not effectively and evenly distribute these medicaments into the body, the indicator system 600 described herein may allow for the receipt of feedback relative to whether the needle is being inserted into a vein instead of an artery.

During insertion, the IR detector may detect any reflected IR light originating from the second light source, capture a signal strength related to the amount of detected light, and send that detected signal strength to a processer to be analyzed. The processor may return to the indicator system 600 data descriptive of where a vein is located by adjusting the state of the arrow indicator 605, the LED indicator 610, or both. When the distal tip 105 of the needle 100 is pointed towards a blood vessel, the signal strength from the reflected IR light may indicate the type of blood vessel in front of the IR camera. In a specific embodiment, the signal strength received at the IR camera may be weaker where the absorption of the IR light by the blood is higher. In some examples, the relative levels of absorbed/reflected light detected (absorption coefficient or reflection coefficient of the emitted light) at the IR camera may indicate whether the blood vessel is a vein or artery due to the level of oxygen present in the blood maintained in these types of blood vessels as described herein. In these embodiments, therefore, the differences in detected light reflected off of internal body parts at one or more different wavelengths may indicate the position of the needle 100 relative to a detected vein. Consequently, in an embodiment, the indicator system 600 may initially direct the clinician to orient the needle 100 towards a blood vessel and subsequently direct the clinician to orient the needle 100 towards a vein rather than an artery.

FIG. 6A shows, specifically, an orientation of the needle 100 relative to a vein in a patient's arm 615. In this specific embodiment, the indicator system 600 shows that the arrow indicator 605 is not pointing straight but is, instead, pointing in a right side of the patient's arm 615. This may indicate to the clinician to direct the distal end of the inserted needle 100 to the right in order to access a vein. Additionally, the LED indicator 610 may concurrently indicate to the clinician as to how deep to project the distal end of the needle 100 into the body of the patient.

FIG. 6B shows, specifically, an orientation of the needle 100 relative to a vein in a patient's arm 615. In this specific embodiment, the indicator system 600 shows that the arrow indicator 605 is pointing straight. This may indicate to the clinician that the direction (x-y orientation) that the distal end of the inserted needle 100 is sufficient in order to access a vein. Additionally, the LED indicator 610 may concurrently indicate to the clinician as to how deep to project the distal end of the needle 100 into the body of the patient.

FIG. 6C shows, specifically, an orientation of the needle 100 relative to a vein in a patient's arm 615. In this specific embodiment, the indicator system 600 shows that the arrow indicator 605 is not pointing straight but is, instead, pointing to a left side of the patient's arm 615. This may indicate to the clinician to direct the distal end of the inserted needle 100 to the left in order to access a vein. Additionally, the LED indicator 610 may concurrently indicate to the clinician as to how deep to project the distal end of the needle 100 into the body of the patient.

In an embodiment, the indicator system 600 described in FIGS. 6A, 6B, and 6C may further include an audio device (not shown) to emit an audio signal to a clinician as an audio indicator. In this embodiment, along with a visual indication, the speaker may indicate the location of a distal tip (not shown) of the needle within the body. By way of example, the audio signal may be a low tone pitch to indicate that the distal tip is not close to a vein while an increasing higher tone pitch indicates that the distal tip has been moved closer to a vein.

Figure 7:
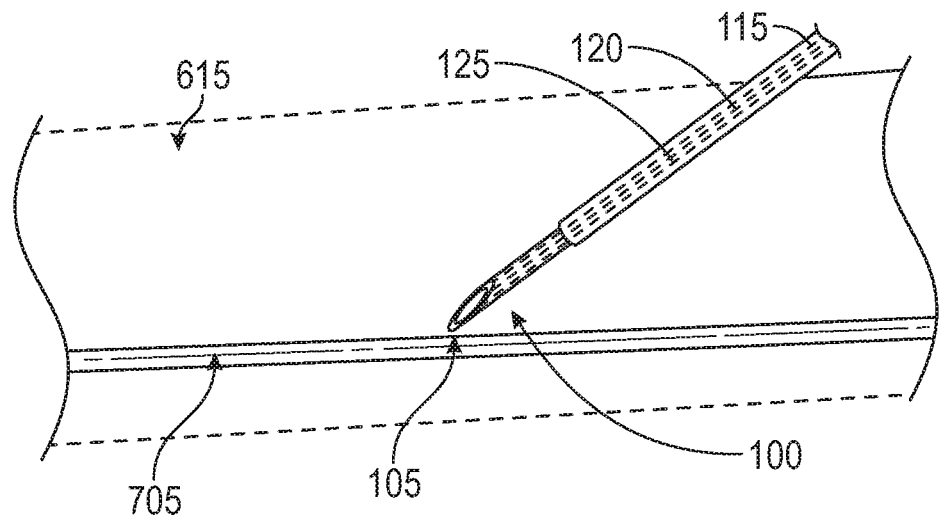
FIG. 7 is a cut-out view of a needle of an intravenous therapy system inserted into an arm of a patient according to some embodiments of the present disclosure.

FIG. 7 is a cut-out view of a needle 100 of an intravenous therapy system inserted into an arm 615 of a patient according to some embodiments of the present disclosure. The cut-out view also shows the IR detector lead 115, the first light source lead 120, and the second light source lead 125 in ghost as dashed lines running up the hollow of the needle 100. As described herein, a clinician may access a vein 705 with the needle 100 by receiving input as to how to direct the distal tip 105 of the needle 100 from the indicator system described herein. The IR detector may receive reflected light originating from either of the first light source or second light source from within the patient's arm 615 as the needle 100 progresses through the patient's arm 615.

Figure 8:
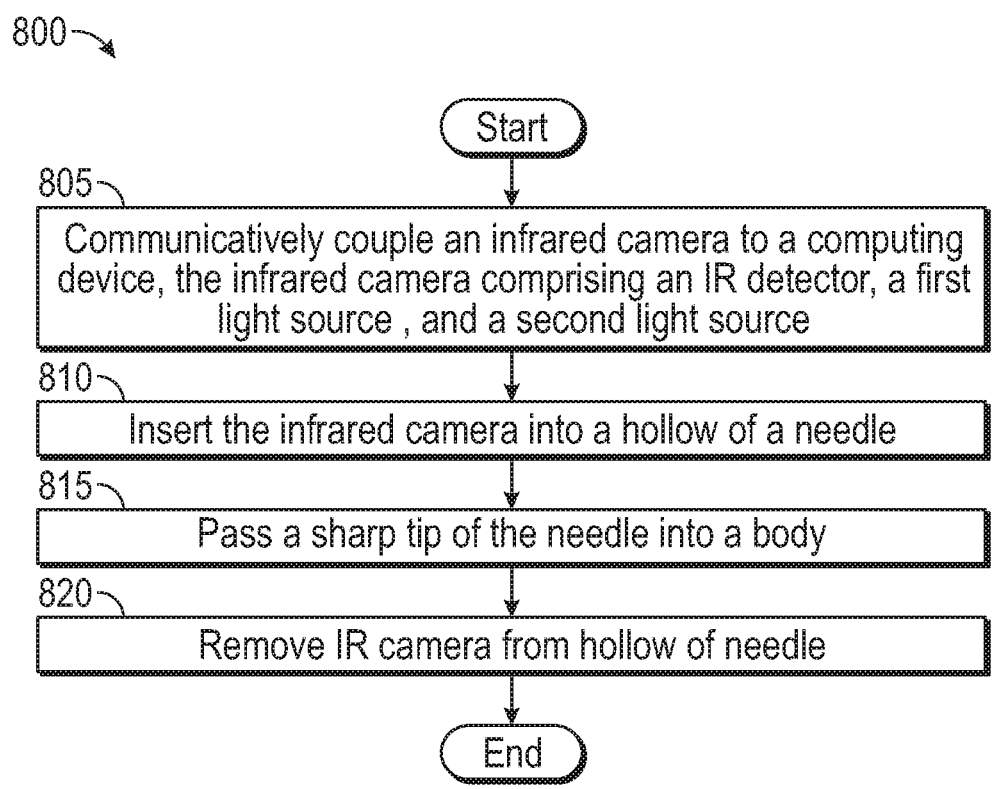
FIG. 8 is a flowchart depicting a method of operating an intravenous therapy system according to some embodiments of the present disclosure.

FIG. 8 is a flowchart depicting a method 800 of operating an intravenous therapy system according to some embodiments of the present disclosure. The method 800 may begin at block 805 with communicatively coupling an infrared camera to a computing device. In an embodiment, the IR camera may include an IR detector, a first light source, and a second light source. The communicative coupling 805 of the IR camera with the computing device may include, in an embodiment, forming a wireless connection with each of the IR detector, a first light source, and a second light. In another embodiment, communicatively coupling 805 the IR camera to the computing device may include completing a wired connection between each of the IR detector, a first light source, and a second light and an electrical/communication port on the computing device.

The method 800 may include, at block 810, inserting the IR camera into a hollow of a needle. The components of the IR camera may be sufficiently small enough to fit within the hollow of the needle. In an embodiment, the components of the IR camera may be selectively removable from the hollow of the needle such as after a vein has been accessed by the needle.

Alternatively, instead of inserting the IR camera into the hollow of the needle, a number of optical fibers, each individually optically coupled to the IR detector, a first light source, and a second light may be inserted into the hollow of the needle. In this embodiment, the size of the components of the IR camera may be independent of the internal diameter of the hollow of the needle. Additionally, the components of the IR camera, in this embodiment, may be coupled directly to a communication port of the computing device or may form part of the computing device.

The method 800 may, in an embodiment, include passing a sharp tip of the needle into a body of a patient at block 815. In this embodiment, the IR camera may be used to access a vein of the patient. The process of accessing the vein through the use of the IR camera includes the use of an indicator system that indicates to a clinician as to the proper orientation of the needle within the patient's body in order to access that vein.

As described herein, an IR camera that includes an IR detector and two distinct IR wavelength or near-IR wavelength emitting diodes may be used to initially scan an area of interest along a patient's body at a near-IR wavelength (e.g., 960 nm) in order to detect a region of low reflected light related to a high absorption of that light indicating the presence of a blood vessel. The IR camera may then switch to emitting a different wavelength of IR light (e.g., 650 to 760 nm). In this embodiment, when the absorption coefficient is increased, the blood vessel detected is a vein. Where the absorption coefficient is decreased, the blood vessel is an artery.

In an embodiment, an initial scan of a scan an area of interest along a patient's body may be done with emitting a wavelength between 650 nm or 760 nm. In this embodiment, the second scan is done with a diode emitting a wavelength of IR light a 960 nm. In this specific embodiment, a detected increase in absorption coefficient would indicate an artery while a detected decrease in absorption coefficient would indicate a vein.

In some embodiments described herein, any initial scan of an area of interest along a patient's body may be conducted before penetrating the patient's skin with the needle 100 as described herein. This may be done where a clinician or other health care provider (HCP) visually detects a superficial vein at the area of interest. If the clinician or other HCP cannot visually detect a vein, the scan can be done after the needle 100 described herein has penetrated the patient's skin. Accordingly, the present specification describes a vein and artery detection device that may be used in both above the patient's skin as well as within the patient's body.

In an embodiment, the orientation of the needle and the IR camera or near-IR camera therein provides a two-dimensional image of the veins and/or arteries in front of the needle. Where the detected blood vessel is not centered in the image, the needle orientation is to be adjusted. Other types of visual, audio, and haptic indicators may be used to indicate the location and presence of the blood vessel being accessed.

In an embodiment, after a vein is accessed by the needle, the method 800 may continue with, at block 820, the removal of the IR camera from within the hollow of the needle. The removal of the IR camera from the hollow of the needle may be done to allow for the passage of fluids such as blood or a medicament therethrough. This embodiment may be completed where the size of the components of the IR camera prevent fluids from passing through the hollow of the needle. In an alternative embodiment, the IR camera may be maintained within the hollow of the needle if the size of the components of the IR camera do not prevent the fluids from passing through the hollow of the needle.

Figure 9:
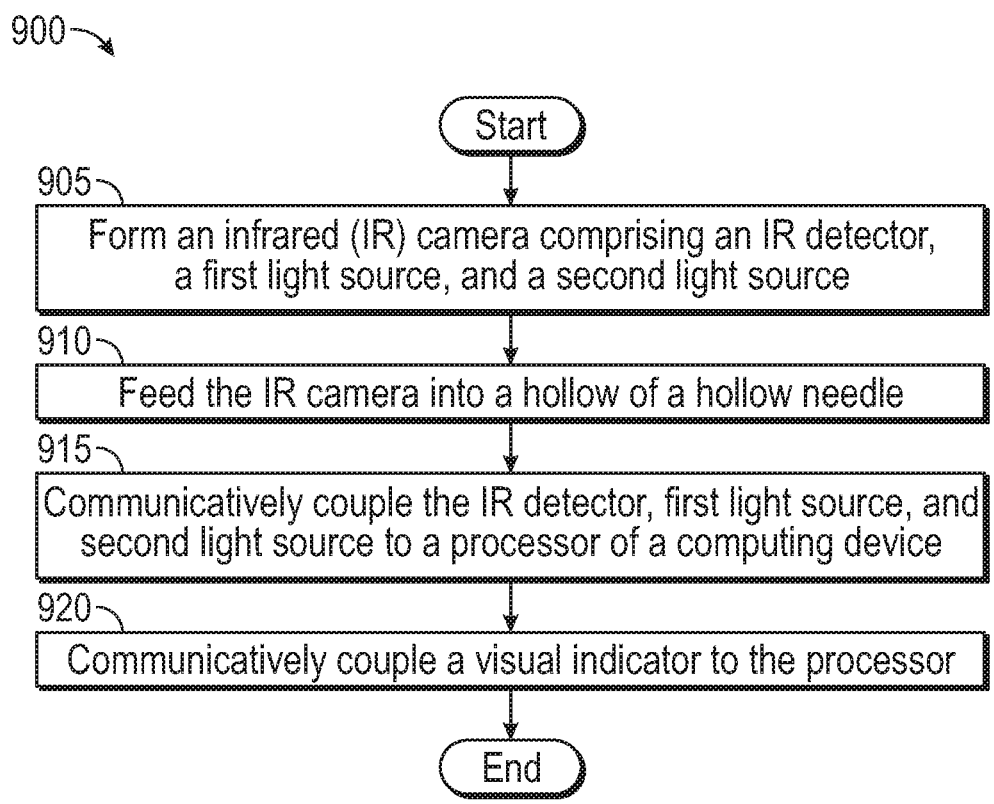
FIG. 9 is a flowchart depicting a method of manufacturing an intravenous therapy system according to some embodiments of the present disclosure.

FIG. 9 is a flowchart depicting a method 900 of manufacturing an intravenous therapy system according to some embodiments of the present disclosure. The method 900 may include, at block 905, forming an IR camera that includes an IR detector, a first light source, and a second light. Each of these components, in an embodiment, may be sized such that the total size of these components may fit within the hollow of a needle. In another embodiment, the IR detector, a first light source, and a second light may each be optically coupled to an individual optical fiber. In this embodiment, the diameters of the optical fibers may be sized such that the total diameter of the three optical fibers fit within the hollow of the needle.

The method 900 may further include, at block 910, feeding the IR camera (or alternatively the optical fibers described herein) into the hollow of the needle. Again, the size of the IR camera or the optical fibers optically coupled to these components may be sized to fit within the hollow of the needle.

The method 900 may further include, at block 915, communicatively coupling the IR detector, the first light source, and the second light source to a processor of a computing device. The computing device may be similar to the information handling system described in connection with FIG. 5 in an embodiment. The communicative coupling at block 915 of the IR detector with the computing device may further include, in an embodiment, electrically coupling the components of the IR camera to the computing device as well to power the IR detector, a first light source, and a second light source.

The method 900, at block 920 may further include communicatively coupling a visual indicator to the processor of the computing device. As described herein, the visual indicator may provide visual feedback to the clinician as to how to adjust the trajectory or orientation of the needle within the patient's body. Further, in an embodiment, the visual indicator may include an audio indicator that emits an audio signal that directs the clinician as to how to orient the needle within the body.

The embodiments described herein provide for an intravenous therapy system that includes an indicator system that facilitates easy visualization of the phase of insertion of the needle into a patient's body while the clinician is physically performing the insertion of the needle. In some embodiments, one or more of the alerts may change or cease in response to one or more of the following: the needle is no longer present in the vein or the needle is no longer fully inserted within the vein.

Again, it is understood that the embodiments of the present application may be combined. As an example, the embodiments of FIGS. 1-9 may be arranged to fit specific uses based on the type of action being conducted. For example, where an artery is to be accessed by the needle, the information handling system may indicate, via the indicator system, a location of the artery while avoiding any veins. This may allow for the introduction of certain medicaments into a specific location in the patient's body without concern for that medicament being distributed throughout the patient's body.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An intravenous therapy system, comprising:
   a hollow needle comprising a distal end and a proximal end, the distal end comprising a sharp tip for insertion into a vein;
   an infrared (IR) camera placed within a hollow portion of the hollow needle, comprising:
      an IR detector;
      a first light source to emit a first wavelength of IR light; and
      a second light source to emit a second wavelength of IR light;
   a comparator to, upon execution of a processor communicatively coupled to the comparator, compare an amount of reflected light received at the IR detector during activation of the first light source and the second light source and provide an indication of light absorption within the vein, wherein the processor is configured to control the IR camera to emit the first wavelength of the IR light at the first light source, to detect a presence of the vein by the comparator, and upon detection of the presence of the vein by the comparator, to control the IR camera to emit the second wavelength of the IR light at the second light source.

2. The intravenous therapy system of claim 1, wherein the IR camera is selectively removable from within the hollow portion of the hollow needle via the proximal end of the hollow needle.

3. The intravenous therapy system of claim 1, further comprising an audio indicator comprising a speaker to provide feedback to a user of the intravenous therapy system indicating an optimal insertion trajectory of the hollow needle into a body based on a detected level of the reflected light by the IR detector.

4. The intravenous therapy system of claim 1, wherein the first light source emits the first wavelength of the IR light between 940 nm and 980 nm.

5. The intravenous therapy system of claim 1, wherein the second light source emits the second wavelength of the IR light between 630 nm and 780 nm.

6. The intravenous therapy system of claim 1, further comprising an arm band communicatively coupled to the comparator, the arm band comprising a visual indicator comprising an indicator light to provide feedback to a user of the intravenous therapy system indicating an optimal insertion trajectory of the hollow needle into a body based on a detected level of the reflected light by the IR detector.

7. A blood vessel detection system comprising:
   a hollow needle comprising:
      a distal end comprising a sharp tip for insertion into a vein; and
      a proximal end comprising an intravenous supply connection;
   an infrared (IR) camera placed within a hollow portion of the hollow needle, comprising:
      an IR detector;
      a first light source to emit a first wavelength of IR light from the hollow portion; and
      a second light source to emit a second wavelength of IR light from the hollow portion;
   a comparator to, upon execution of a processor communicatively coupled to the comparator, compare an amount of reflected light received at the IR detector during activation of the first light source and the second light source and provide an indication of light absorption within the vein;
   an audio indicator communicatively coupled to the comparator comprising a speaker to provide feedback to a user of the blood vessel detection system indicating an optimal insertion trajectory of the hollow needle into a body based on the detected amount of the reflected light received at the IR detector, wherein the processor is configured to control the IR camera to emit the first wavelength of the IR light at the first light source and, upon detection of a presence of the vein by the comparator, to control the IR camera to emit the second wavelength of the IR light at the second light source.

8. The blood vessel detection system of claim 7, wherein the IR camera is selectively removable from within the hollow portion of the hollow needle via the proximal end of the hollow needle.

9. The blood vessel detection system of claim 7, wherein the first light source emits the first wavelength of the IR light between 940 nm and 980 nm.

10. The blood vessel detection system of claim 7, wherein the second light source emits the second wavelength of the IR light between 630 nm and 780 nm.

11. The blood vessel detection system of claim 7, further comprising an arm band communicatively coupled to the comparator, the arm band comprising a visual indicator comprising an indicator light to provide feedback to the user of the blood vessel detection system indicating the optimal insertion trajectory of the hollow needle into a body based on a detected level of the reflected light by the IR detector.

12. The blood vessel detection system of claim 7, wherein the comparator compares the amount of the reflected light received at the IR detector to differentiate between the vein and an artery within the body and indicates, via the audio indicator, a location of the vein within the body.

13. A blood vessel detection system comprising:
a hollow needle comprising:
a distal end comprising a sharp tip for insertion into a vein; and
a proximal end comprising an intravenous supply connection;
an infrared (IR) camera placed within a hollow portion of the hollow needle, comprising:
an IR detector;
a first light source to emit a first wavelength of IR light from the hollow portion; and
a second light source to emit a second wavelength of IR light from the hollow portion;
a comparator to, upon execution of a processor communicatively coupled to the comparator, compare an amount of reflected light received at the IR detector during activation of the first light source and the second light source and provide an indication of light absorption within the vein;
an arm band communicatively coupled to the comparator, the arm band comprising a visual indicator comprising an indicator light to provide feedback to a user of the blood vessel detection system indicating an optimal insertion trajectory of the hollow needle into a body based on a detected level of the reflected light by the IR detector, wherein the processor is configured to control the IR camera to emit the first wavelength of the IR light at the first light source and, upon detection of a presence of the vein by the comparator, to control the IR camera to emit the second wavelength of the IR light at the second light source.

14. The blood vessel detection system of claim 13, wherein the IR detector comprises a photodiode optically coupled to an optical fiber passed through the hollow portion of the hollow needle.

15. The blood vessel detection system of claim 13, wherein the first light source further comprises a first light-emitting diode (LED) optically coupled to an optical fiber passed through the hollow portion of the hollow needle.

16. The blood vessel detection system of claim 13, wherein the second light source further comprises a second light-emitting diode (LED) optically coupled to an optical fiber passed through the hollow portion of the hollow needle.

* * * * *